Figure 1:
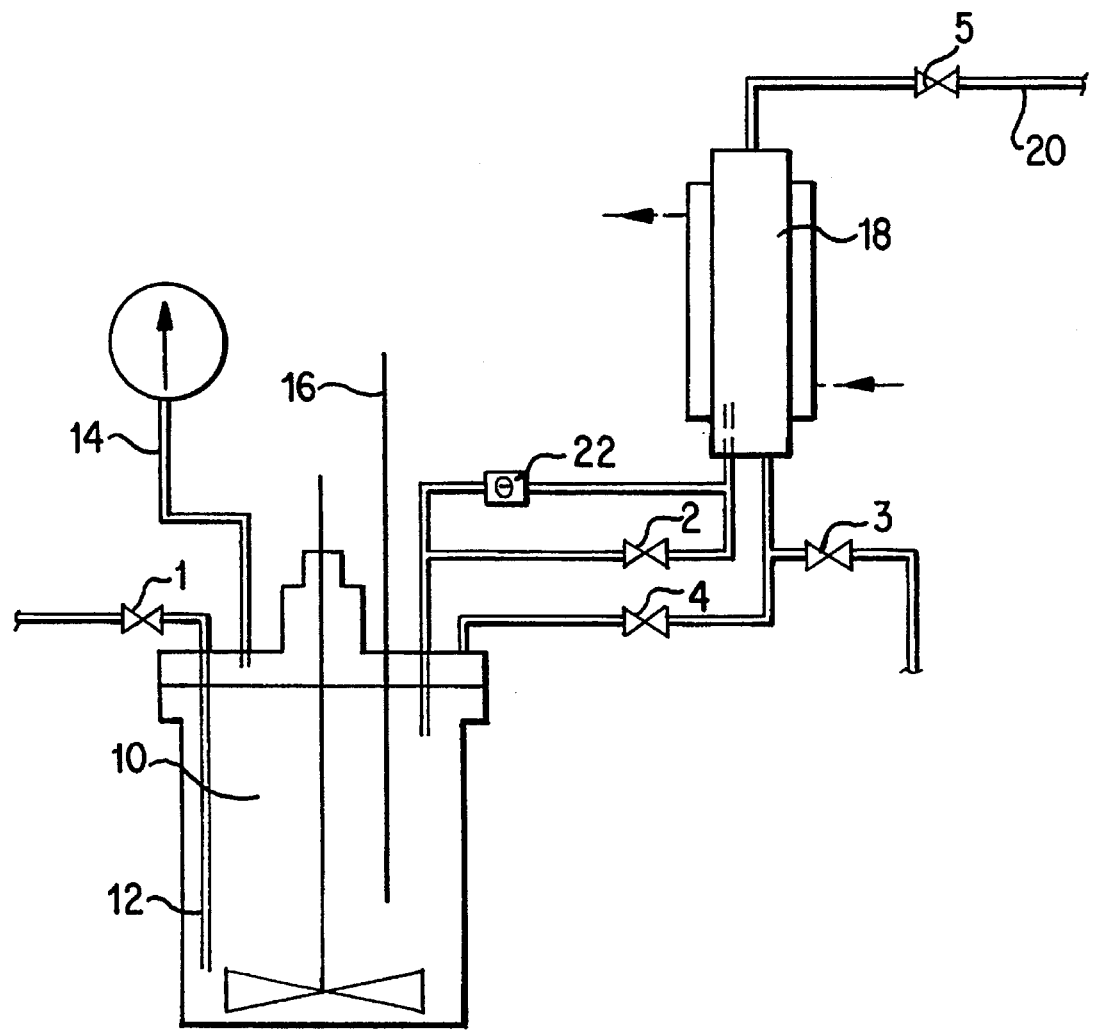

United States Patent [19]
Friis et al.

[11] Patent Number: 5,591,857
[45] Date of Patent: Jan. 7, 1997

[54] PROCESS FOR THE PREPARATION OF 2,3,5,6-TETRACHLOROPYRIDINE

[75] Inventors: Niels Friis, Bækmarksbro; Per Frølich, Harboør, both of Denmark

[73] Assignee: Cheminova Agro A/S, Ronland, Denmark

[21] Appl. No.: 290,946

[22] PCT Filed: Dec. 1, 1993

[86] PCT No.: PCT/DK93/00392

§ 371 Date: Aug. 22, 1994

§ 102(e) Date: Aug. 22, 1994

[87] PCT Pub. No.: WO94/14774

PCT Pub. Date: Jul. 7, 1994

[30] Foreign Application Priority Data

Dec. 22, 1992 [DK] Denmark ................... 1535/92

[51] Int. Cl.⁶ .................. C07D 213/61; C07D 213/69
[52] U.S. Cl. .................................................. 546/296
[58] Field of Search ................................ 546/296

[56] References Cited

U.S. PATENT DOCUMENTS 4,360,676  11/1982  Martin et al. ..................... 546/243

*Primary Examiner*—C. Warren Ivy
*Assistant Examiner*—D. Margaret M. Mach
*Attorney, Agent, or Firm*—Evenson, McKeown, Edwards & Lenahan, P.L.L.C.

[57] ABSTRACT

An improved process for the preparation of 2,3,5,6-tetrachloropyridine of the formula

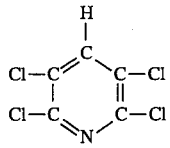

consists in that 3,3,5-trichloroglutarimide of the formule

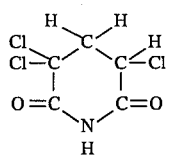

is reacted either
  a. with phosphorus trichloride or phosphorus oxytrichloride or mixtures thereof in the presence from the start of catalytic amounts of hydrogen chloride, followed by a conversion of polyphosphorous compounds formed into phosphorus oxytrichloride by supplying chlorine, optionally only after supplying further phosphorus trichloride, or
  b. with phosphorus trichloride and chlorine, optionally in the presence of phosphorus oxytrichloride as a solvent, followed by a dehydrochlorination of the reaction mixture and finally conversion of polyphosphorus compounds formed into phosphorus oxytrichloride by supplying chlorine, optionally only after supplying further phosphorus trichloride.

Improved yields of a purer product are obtained.

14 Claims, 2 Drawing Sheets

PROCESS FOR THE PREPARATION OF 2,3,5,6-TETRACHLOROPYRIDINE

This application is a 371 of PCT/DK93/00392, filed Dec. 1, 1993.

The present invention relates to an improved process for the preparation of 2,3,5,6-tetrachloropyridine of formula I

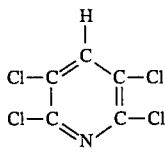

from 3,3,5-trichloroglutarimide of formula II

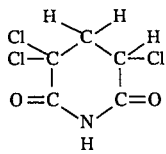

2,3,5,6-Tetrachloropyridine is a useful intermediate product in the preparation of various herbicides, fungicides and insecticides, e.g., (3,5,6-trichloro-2-pyridyloxy)acetic acid [BR patent No. 74,02900] and O,O-diethyl-O-3,5,6-trichloro-2-pyridylphosphorothioate [U.S. Pat. No. 3,244,586].

Various processes for the preparation of 2,3,5,6-tetrachloropyridine (I) are known, including the following:

2,3,5,6-Tetrachloropyridine can be prepared from glutarimide by chlorination with phosphorus pentachloride. Thereby, a mixture of chlorinated pyridines is formed which can then be further chlorinated with chlorine to 2,3,4,5,6-pentachloropyridine which can thereafter be selectively reduced by zinc to 2,3,5,6-tetrachloropyridine.

2,3,5,6-Tetrachloropyridine can also be prepared by chlorination of pyridine or pyridine derivatives as, e.g., 2,6-dichloropyridine, α-picoline or 3,5-dichloro-2-trichloromethylpyridine in a vapour phase at a high temperature.

The starting material can also be glutaric acid dinitrile, pentenenitrile, ε-caprolactam or cyclohexanone oxime which by chlorination at a high temperature (400°–600° C.) can be converted into 2,3,5,6-tetrachloropyridine.

These high-temperature processes are usually not selective as they likewise result in the formation of other highly chlorinated by-products which are to be removed.

One such by-product is 2,3,4,5,6-pentachloropyridine which as mentioned can be converted, however, into 2,3,5,6-tetrachloropyridine by selective reduction of the chlorine atom in the 4-position.

3,5,6-Trichloropyridin-2-ol or mixtures thereof with 2,3,5,6-tetrachloropyridine can be prepared from trichloroacetyl chloride and acrylonitrile.

These processes primarily concern the preparation of 3,5,6-trichloropyridin-2-ol, and tetrachloropyridine is a by-product in the application of the procedures.

Trichloropyridinol is preferably used for the preparation of O,O-diethyl-O-3,5,6-trichloro-2-pyridylphosphorothioate, whereas tetrachloropyridine has a wider field of application, including, inter alia, the preparation of the above-mentioned phosphorothioate via hydrolysis of tetrachloropyridine to trichloropyridinol.

2,3,5,6-Tetrachloropyridine can be prepared from 3,3,5-trichloroglutarimide by reaction with phosphorus trichloride, phosphorus oxytrichloride or phosphorus pentachloride.

The present invention relates to an improved process for the preparation of 2,3,5,6-tetrachloropyridine (I) from 3,3,5-trichloroglutarimide (II), and said process is characterized in that the 3,3,5-trichloroglutarimide is reacted either a. with phosphorus trichloride or phosphorus oxytrichloride or mixtures thereof in the presence from the start of catalytic amounts of hydrogen chloride, followed by a conversion of polyphosphorus compounds formed into phosphorus oxytrichloride by supplying chlorine, optionally only after supplying further phosphorus trichloride, or b. with phosphorus trichloride and chlorine, optionally in the presence of phosphorus oxytrichloride as a solvent, followed by a dehydrochlorination of the reaction mixture and finally conversion of polyphosphorus compounds formed into phosphorus oxytrichloride by supplying chlorine, optionally only after supplying further phosphorus trichloride.

Use can be made of various expedient embodiments of process a. of the invention as stated in claims 2–7.

The reaction of 3,3,5-trichloroglutarimide (II) with phosphorus trichloride or phosphorus oxytrichloride or mixtures thereof by process a. of the invention, which is preferably carried out at 160° C. to 200° C. for, e.g., ½ to 3 hours, takes place substantially according to the reaction scheme:

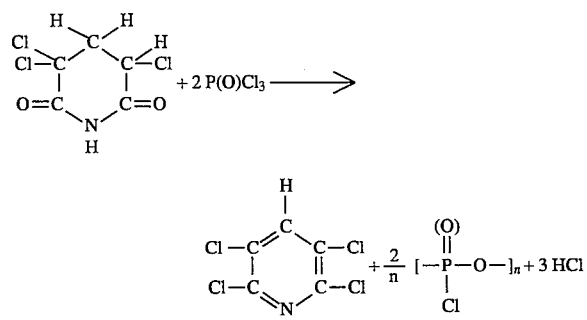

It has surprisingly been found that the latter process proceeds only in the presence of catalytic amounts of hydrogen chloride from the start of the reaction.

The hydrogen chloride can be supplied to the reaction mixture in the form of dry hydrogen chloride gas, or it can be formed from the reaction between phosphorus trichloride or phosphorus oxytrichloride and water present in the reaction mixture, possibly from water content in the trichloroglutarimide.

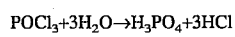

During the reaction 3,3,5-trichloroglutarimide is converted into 2,3,5,6-tetrachloropyridine, and about 2 moles of phosphorus (as phosphorus trichloride and/or phosphorus oxychloride) per mole of trichloroglutarimide used are bound as a polyphosphorus compound which precipitates in the reaction mixture as a highly viscous to glassy compound.

The hydrogen chloride formed during the reaction can be vented through a back-pressure valve on the reaction vessel such as to keep the pressure in the vessel at an overpressure of between 10 bars and 15 bars (gauge) during the reaction.

Phosphorus trichloride can subsequently be added to the reaction mixture at 50° C. to 100° C. such that the amount of phosphorus trichloride used is higher than or equal to 2 moles per mol of 3,3,5-trichloroglutarimide used.

Thereafter, 2 moles of chlorine per mole of 3,3,5-trichloroglutarimide used can be supplied, and the reaction mixture is heated at reflux [about 100° C.] for 1 hour.

During the last reaction, polyphosphorus compounds formed are converted into phosphorus oxytrichloride.

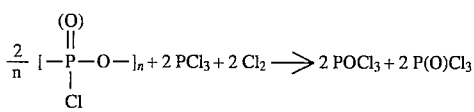

Thereby, the reaction mixture becomes homogeneous at an elevated temperature (about 50° C.).

Process b. of the invention which is suitable for continuous operation consists in a chlorination of 3,3,5-trichloroglutarimide with phosphorus trichloride and chlorine, appropriately at 20° C. to 100° C., preferably at 50° C. to 70° C., followed by heating the reaction mixture to appropriately between 160° C. and 200° C. for ½ to 3 hours. After cooling the reaction mixture, remaining polyphosphorus compounds are converted into phosphorus oxytrichloride by treatment with chlorine, optionally only after supplying further phosphorus trichloride.

The reaction of 3,3,5-trichloroglutarimide (II) with phosphorus trichloride and chlorine takes places substantially according to the reaction schemes:

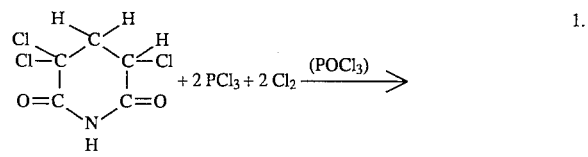

1.

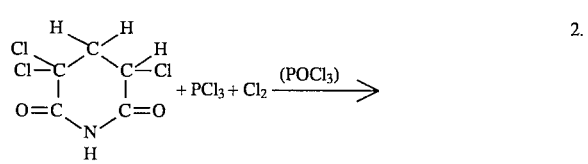

2.

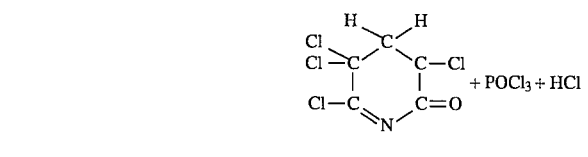

3.

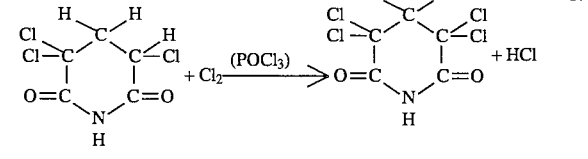

4.

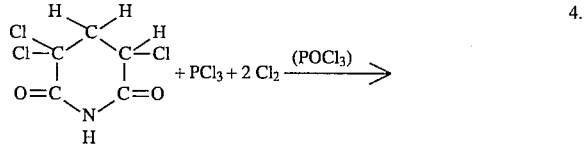

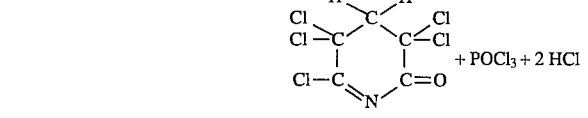

Reactions 1 and 2 are desirable as the intermediates therefrom by heating to appropriately between 160° C. and 200° C. turn into 2,3,5,6-tetrachloropyridine (I).

Reactions 3 and 4 are undesirable as the intermediates therefrom are not converted by the subsequent heating. Thereby, these intermediates constitute a yield loss in the process as well as a possible source of contamination of the end product 2,3,5,6-tetrachloropyridine.

By carrying out a partial chlorination wherein less than 2 moles of chlorine per mole of 3,3,5-trichloroglutarimide [m<2] are used, reactions 3 and 4 can be suppressed in favour of the essential main reaction:

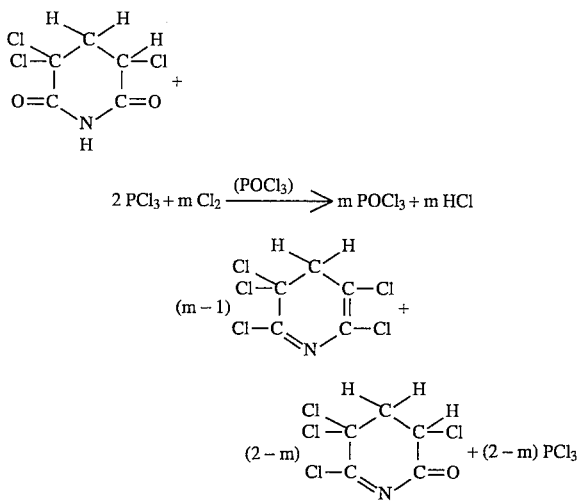

Use can be made of various expedient embodiments of process b. of the invention as stated in claims 8–16.

In this first part of the chlorination reaction, preferably between 1.2 and 1.8 moles of chlorine per mole of 3,3,5-trichloroglutarimide are used.

Besides the above-mentioned intermediates, the reaction mixture after the chlorination may possibly contain unreacted 3,3,5-trichloroglutarimide.

Thereafter, the reaction mixture is appropriately heated to between 160° C. and 200° C. whereby a dehydrochlorination and exchange of the last carbonyl oxygen by chlorine take place, proceeding substantially according to the reaction scheme:

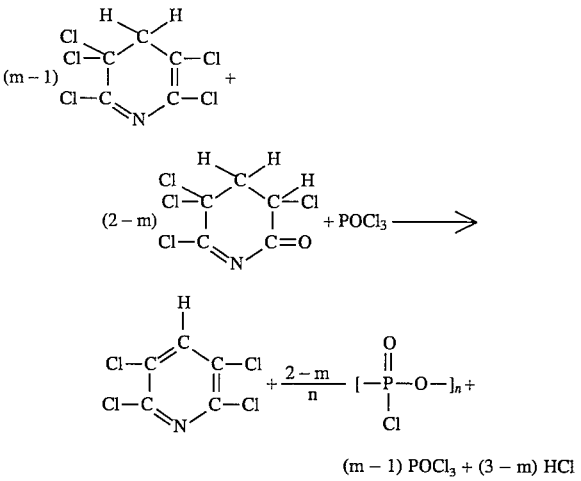

The reaction mixture from the chlorination contains sufficient dissolved hydrogen chloride to catalyze the dehydrochlorination which takes place by the heating to appropriately between 160° C. and 200° C.

During the heating with phosphorus trichloride or phosphorus oxytrichloride or mixtures thereof, any unreacted 3,3,5-trichloroglutarimide will be converted into 2,3,5,6-tetrachloropyridine (I) as previously described.

After cooling the reaction mixture to between 50° C. and 100° C., said mixture remains homogeneous, the small amounts of polyphosphorus compounds occurring dissolved in the reaction mixture.

Conversion of these polyphosphorus compounds into phosphorus oxytrichloride can take place as previously described by an aftertreatment with chlorine.

The amount of chlorine to be used for the after-chlorination is the amount of chlorine needed to attain a total consumption of 2 moles of chlorine per mole of 3,3,5-trichloroglutarimide used.

Work up of the reaction mixture can take place by distillation in that phosphorus trichloride and phosphorus oxytrichloride can initially be distilled off at atmospheric pressure to a bottom temperature of about 140° C. Thereafter, vacuum is applied to about 20 mm Hg, and 2,3,5,6-tetrachloropyridine can be distilled off at about 140° C.

A number of analogous processes for the preparation of chloropyridines are known from the literature:

H. J. Den Hartog and J. De Bruyn, Recueil 70 (1951) pp. 182–90 describe the conversion of 2-hydroxy-3,5,6-trichloropyridine into 2,3,5,6-tetrachloropyridine by heating with phosphorus oxytrichloride. The polyphosphorus compounds formed are decomposed with water before the product is steam distilled.

U.S. Pat. No. 4,225,716 describes the conversion of 2,6-dihydroxypyridine compounds into the corresponding 2,6-dichloropyridine compounds with phosphorus oxytrichloride in the presence of a basic nitrogen compound, e.g. quinoline.

Also here polyphosphorus compounds (possibly quinoline-phosphorus complexes) are decomposed with water before work up of the product.

Similar processes are described in the following patents: DD 154,538, DE 2,127,521, DE 2,306,045, DE 2,307,444, U.S. Pat. No. 2,742,478 and U.S. Pat. No. 2,742,479.

A common feature of the described processes is the fact that the starting material is an aromatic compound and that the polyphosphorus compounds formed and any phosphorus-amine complexes are decomposed with water before a work up of the product.

Nature, Vol. 210, Apr. 30, 1966 pp 523–24; J. Labelled Comp. and Radiopharmaceuticals, Vol. XVIII, No. 5, 1981 pp. 629–41; J. Agr. Food Chem. 15, No. 3, 1967 pp. 508–11 and J. Am. Chem. Soc. 65, 1943 pp. 270–2 describe the conversion of glutarimide into chloropyridine compounds.

The preparation takes place by melting glutarimide with phosphorus pentachloride or by reacting glutarimide with phosphorus pentachloride in phosphorus trichloride. Nature describes that if phosphorus oxytrichloride is used as a solvent, no chlorinated pyridines are formed.

Helvetica Chimica Acta, Vol. 59, 1976 pp. 179–190 describes the preparation of halogenated pyridines from substituted glutarimides by treatment with phosphorus pentachloride or phosphorus oxytrihalogenide.

The work up in the above-mentioned processes takes place by decomposing residual phosphorus trichloride, phosphorus oxytrichloride and phosphorus pentachloride with water, optionally by pouring onto ice.

U.S. Pat. No. 4,360,676 describes a similar process wherein 3,3,5-trichloroglutarimide in N,N-dimethylformamide is reacted to 2,3,5,6-tetrachloropyridine with phosphorus pentachloride.

If said process is used, it is not possible to regenerate all solvent used. It is also not possible to regenerate the phosphorus compounds used since phosphorus pentachloride as well as phosphorus oxychloride react with N,N-dimethylformamide and result in phosphorylated products which are to be decomposed with water before the tetrachloropyridine is worked up.

U.S. Pat. No. 4,360,676 does not state the yield of 2,3,5,6-tetrachloropyridine in said process, but a similar process performance without the use of a solvent, and with the use of phosphorus trichloride or phosphorus oxytrichloride as a solvent is described in Example 1 below.

In the following comparative experiments (Example 1) a substantial part of the trichloroglutarimide used is converted into 3,3,5,5-tetrachloroglutarimide which reduces the yield and contaminates the end product.

U.S. Pat. No. 4,360,676 also indicates a method for the conversion of 3,3,5-trichlorglutarimide into 2,3,5,6-tetrachloropyridine by heating trichloroglutarimide in phosphorus oxytrichloride. In both of the examples stated, residual phosphorus compounds are decomposed with water (ice or steam). The yield of 2,3,5,6-tetrachloropyridine from 3,3,5-trichloroglutarimide is stated in one example to be about 85%.

In a comparative example (Example 2) stated below it is shown that completely dry trichloroglutarimide does not react—even after a long time of heating—with phosphorus oxytrichloride, whereas even small amounts of water or dry hydrogen chloride immediately activate the reaction.

The improved process of the invention for the preparation of 2,3,5,6-tetrachloropyridine has the following advantages over prior art procedures:

a. In relation to the use of the starting materials glutarimide, pyridine, pyridine derivatives, glutaric acid dinitrile, pentenenitrile, $\epsilon$-caprolactam, cyclohexanone oxime and trichloroacetyl chloride coupled with acrylonitrile, there is obtained a selective preparation of the product (product purity >99%) in a yield >95%.

b. In relation to what is described in U.S. Pat. No. 4,360,676, there is obtained an improved yield as well as the advantage of the phosphorus compound used being regenerable in the form of phosphorus oxytrichloride which is a valuable by-product in the tetrachloropyridine production.

c. In relation to what is described in U.S. Pat. No. 4,360,676, there is obtained an improved process performance by using a partial chlorination and subsequent dehydrochlorination followed by a final chlorination, which improved process performance opens up the possibility of a continuous process performance since no precipitation of polyphosphorus compounds occurs.

d. In relation to what is described in U.S. Pat. No. 4,360,676 there is obtained an environmentally improved process, since in the improved process only a slight amount of distillation residue results, whereas in the process described in U.S. Pat. No. 4,360,676 a major aqueous phase containing phosphorus compounds results.

FIG. 1 Autoclave arrangement for preparing 2,3,5,6-tetrachloropyridine.

Figure 2:
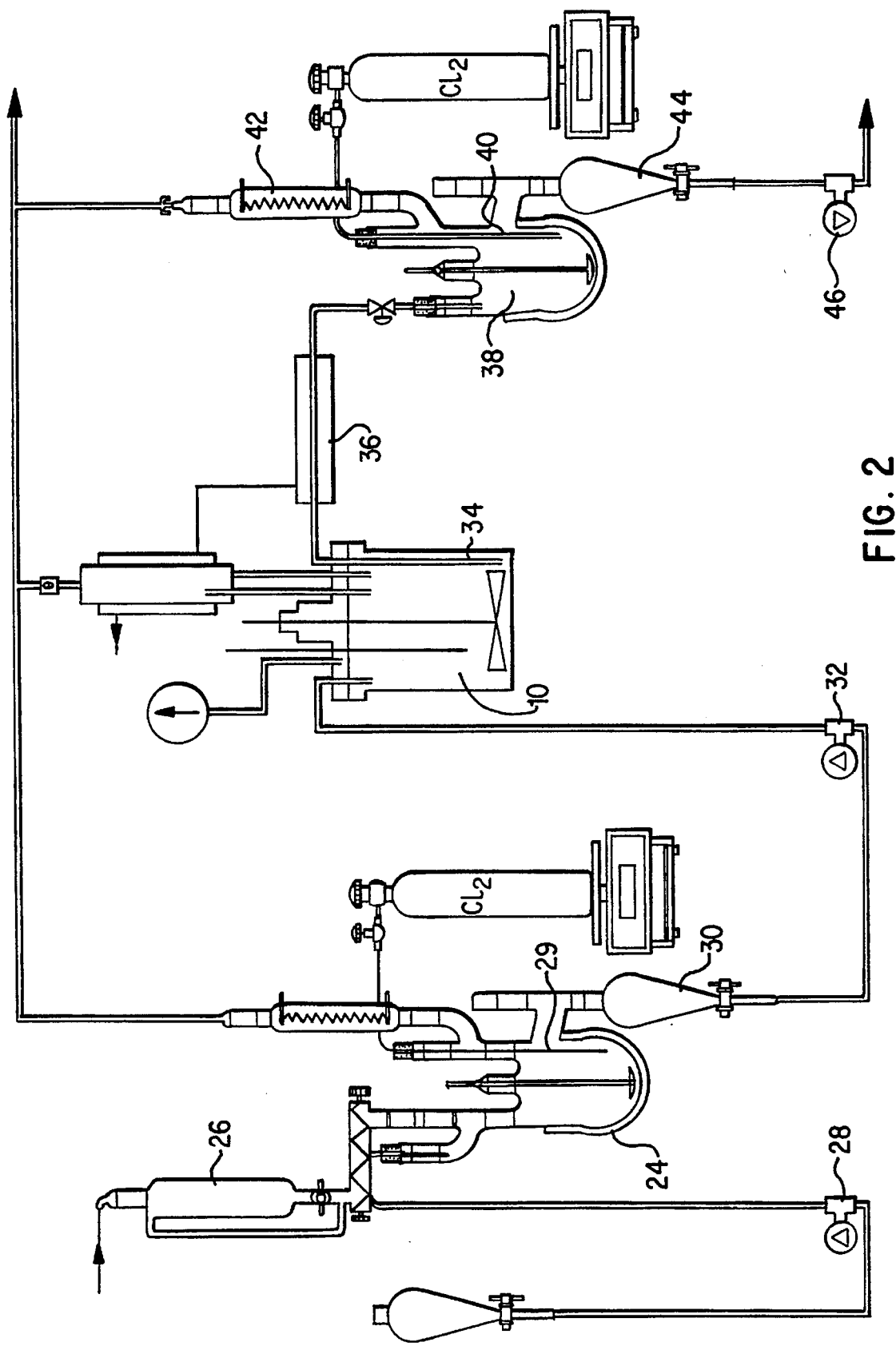

FIG. 2 Laboratory arrangement for continuously preparing 2,3,5,6-tetrachloropyridine.

The improved process of the invention for the preparation of 2,3,5,6-tetrachloropyridine is illustrated by the following Examples 3–5. Examples 1–2 are comparative examples and not examples of the process of the invention.

EXAMPLE 1

Comparative examples using phosphorus pentachloride.
Experiment 1.

11 g (0.05 mol) of trichloroglutarimide and 23 g (0.11 mol) of phosphorus pentachloride are mixed and melted at 100° to 120° C.

At about 100° C. a vigorous exothermic reaction takes place, and the temperature increases to about 140° C. where phosphorus oxytrichloride formed begins to reflux.

The temperature is maintained at reflux for 2 hours and thereafter the reaction mixture is poured onto crushed ice.

From the aqueous phase 15.2 g of solid is isolated, which is found to contain:

5.9% of 2,3,5,6-tetrachloropyridine, 2.3% of 3,5,6-trichloropyridin-2-ol and 4.6% of 3,3,5,5-tetrachloroglutarimide.

Experiment 2.

In order to avoid a vigorous exothermic reaction wherein all phosphorus pentachloride reacts instantaneously, phosphorus trichloride is used instead, to which gaseous chlorine is instantaneously supplied.

Phosphorus trichloride and chlorine react instantaneously to phosphorus pentachloride which thereafter reacts with the starting material.

By controlling the chlorine metering rate, the reaction rate and thereby the heat generation from the process can be controlled.

11 g (0.05 mol) of trichloroglutarimide and 27.5 g (0.20 mol) of phosphorus trichloride are heated to about 50° C. and at this temperature there is supplied:

0.7 g (0.10 mol) of chlorine.

After the metering of chlorine is complete, the reaction mixture is heated at reflux for 2 hours. Thereafter phosphorus trichloride og phosphorus oxytrichloride are distilled off and the reaction mixture is then poured onto crushed ice.

From the aqueous phase 5.4 g of solid is isolated, which is found to contain:

9.6% of 2,3,5,6-tetrachloropyridine, 23.4% of 3,5,6-trichloropyridin-2-ol and 20.6% of 3,3,5,5-tetrachloroglutarimide.

Experiment 3.

11 g (0.05 mol) of trichloroglutarimide, 13.8 g (0.10 mol) of phosphorus trichloride and 15.4 g (0.10 mol) of phosphorus oxytrichloride are heated to about 50° C. and at this temperature there is supplied:

0.7 g (0.10 mol) of chlorine.

After the metering of chlorine is complete, the reaction mixture is heated at reflux for 2 hours. Thereafter phosphorus trichloride and phosphorus oxytrichloride are distilled off and the reaction mixture is then poured onto crushed ice.

From the aqueous phase 7.0 g of solid is isolated, which is found to contain:

68.5% of 2,3,5,6-tetrachloropyridine, 13.4% of 3,5,6-trichloropyridin-2-ol and 13.4% af 3,3,5,5-tetrachloroglutarimide.

EXAMPLE 2

Comparative example using hydrogen chloride as an activator for the process.
Experiment 1.

11 g (0.05 mol) of trichloroglutarimide which has been recrystallized twice from methanol and vacuum-dried [water analysis shows<0.01%] and 30.7 g (0.20 mol) of phosphorus oxytrichloride are heated in an autoclave at 180° C.

The pressure in the autoclave shows at 180° C. a overpressure of about 8 bars (gauge). After a reaction time of 8 hours at 180° C. no increase of the pressure in the autoclave has occurred.

Evaporation of the reaction mixture to dryness and analysis of the residue show only a content of trichloroglutarimide.

Experiment 2.

11 g (0.05 mol) of trichloroglutarimide which has been recrystallized twice from methanol and vacuum-dried [water analysis shows <0.01%] and 30.7 g (0.20 mol) of phosphorus oxytrichloride are mixed in an autoclave.

From a pressurized hydrogen chloride cylinder a hydrogen chloride overpressure of 0.1 bar (gauge) is applied to the autoclave which is then heated at 180° C.

The pressure in the autoclave shows at 180° C. an overpressure of 8 bars (gauge), but then it increases rapidly and at an overpressure of 12 bars (gauge) hydrogen chloride formed is vented to an overpressure of about 10 bars (gauge).

The pressure in the autoclave is kept at an overpressure of between 10 and 12 bars (gauge) by frequently venting hydrogen chloride formed. After a reaction time of about ½ hour at 180° C. the pressure does not increase any longer, and after a reaction time of 1 hour the heating is interrupted.

After cooling the autoclave, excess of phosphorus oxytrichloride is distilled off and crushed ice is added to the residue.

From the aqueous phase 10.5 g of dried product is isolated which by analysis is found to contain 89.5% of 2,3,5,6-tetrachloropyridine.

No other organic compounds can be traced in the product and a phosphorus analysis of the product does show that the remaining 10.5% of the product consists of inorganic phosphorus compounds.

Experiment 3.

To 11 g (0.05 mol) of trichloroglutarimide which has been recrystallized twice from methanol and vacuum-dried water analysis shows <0.01%, 0.05 g of water is added whereafter it is mixed with:

30.7 g (0.20 mol) of phosphorus oxytrichloride in an autoclave.

By heating to 180° C. in the autoclave an increase of pressure immediately occurs above the overpressure of 8 bars (gauge) provided by the phosphorus oxytrichloride at the reaction temperature. As in Experiment 2 it is necessary to vent hydrogen chloride formed from the autoclave several times during the first half an hour of reaction.

The work up is carried out as described in Experiment 2, and the results of the experiment are comparable to those of said experiment.

Experiment 4.

Trichloroglutarimide prepared by precipitation from an aqueous solution frequently contains residual water after drying.

A trichloroglutarimide product prepared in such way and vacuum-dried at 40° C. for 12 hours is analysed for water content. Left in the product about 0.5% of water remains.

If such a product is heated with phosphorus oxytrichloride in an autoclave at 180° C. as described in Experiment 3, an analogous course of reaction to that described in Experiment 3 takes place.

EXAMPLE 3

Preparation of 2,3,5,6-tetrachloropyridine

In the following experiments the improved process a. of the invention for the preparation of 2,3,5,6-tetrachloropyridine is illustrated.

As starting material in the experiments described use is made of a self-produced 3,3,5-trichloroglutarimide which has been dried to a residual content of water of between 0.5 and 1%.

The starting materials are mixed in a 1 liter autoclave 10 as outlined in FIG. 1 of the drawings. The autoclave is closed and heated to the reaction temperature.

Vented hydrogen chloride is collected in a scrubber with water and the amount of vented hydrogen chloride is determined by titration.

After the reaction is complete, the autoclave is cooled and a sample of the content is analyzed for content of phosphorus trichloride and phosphorus oxytrichloride in order to determined the amount bound as polyphosphorus compounds.

Thereafter phosphorus trichloride is optionally added, the reaction mixture is heated to about 50° C. and through the submerged pipe 12 chlorine is supplied from a pressurized cylinder.

After the metering of chlorine is complete, the reaction mixture is heated at reflux for 1 hour. Thereafter phosphorus trichloride and phosphorus oxytrichloride are distilled off at atmospheric pressure to a-bottom temperature of about 140° C.

Vacuum is gradually applied to the system through line 14 while continuously distilling off phosphorus oxytrichloride. At a vacuum of about 20 mm Hg and a continued bottom temperature of 140° C. the 2,3,5,6-tetrachloropyridine is distilled off. The temperature is detected by thermosensor 16.

While distilling off the product there is cooled with oil in a cooler 18 at a temperature of 100° C. in order to prevent the product from crystallizing. The product is then sent to the hydrogen chloride absorber through line 20.

Moreover, concerning the autoclave arrangement for the preparation of 2,3,5,6-tetrachloropyridine as shown in FIG. 1 of the drawings the following should be remarked.

The back-pressure valve 22, can be set to open at pressures of between 10 and 15 bars (gauge).

During the reaction between trichloroglutarimide and phosphorus trichloride and/or phosphorus oxytrichloride, valves 1, 2, 3 and 4 are closed, and valve 5 is open.

While supplying chlorine, valves 1, 2, 4 and 5 are open, and valve 3 is closed. While distilling off phosphorus trichloride and phosphorus oxytrichloride, valves 2, 3 and 5 are open, and valves 1 and 4 are closed. While distilling off tetrachloropyridine (vacuum distillation), valves 2 and 3 are open, and valves 1, 4 and 5 are closed.

During the reaction—up to distilling off tetrachloropyridine—the condenser is cooled with oil at 0° C.

While distilling off tetrachloropyridine, there is cooled with oil at 100° C.

The results of 5 experiments with varying ratios of phosphorus trichloride to phosphorus oxytrichloride are shown in the following Table 1.

As appears from Table 1, 2,3,5,6-tetrachloropyridine is obtained by process a. of the invention in a high yield and with high purity.

TABLE 1

| | | Experiment | | | | |
|---|---|---|---|---|---|---|
| | | 1 | 2 | 3 | 4 | 5 |
| Starting materials: | | | | | | |
| 3,3,5-trichloro-glutarimide | mol | 1.0 | 1.0 | 1.0 | 1.0 | 1.0 |
| phosphorus trichloride | mol | 4.0 | 2.0 | 1.0 | 0 | 0 |
| phosphorus oxytrichloride | mol | 0 | 2.0 | 2.0 | 3.0 | 4.0 |
| Reaction temperature | °C. | 180 | 180 | 180 | 180 | 180 |
| Reaction time | hours | 3 | 3 | 3 | 1 | 1 |
| Reaction pressure | bars (gauge) | 15 | 15 | 15 | 10 | 10 |
| Collected hydrogen chloride | mol | 1.9 | 1.9 | 1.9 | 1.9 | 1.9 |
| Phosphorus bound as polyphosphorus comp. | mol | 1.8 | 2.0 | 2.6 | 2.4 | 2.2 |
| Further added phosphorus trichloride | mol | 0 | 0 | 1.0 | 2.0 | 2.0 |
| Chlorine supplied | mol | 2.0 | 2.0 | 2.0 | 2.0 | 2.0 |
| Distilled off: | | | | | | |
| phosphorus trichloride | mol | 2.0 | 0 | 0 | 0 | 0 |
| phosphorus oxytrichloride | mol | 1.8 | 3.75 | 3.8 | 4.9 | 5.9 |
| 2,3,5,6-tetrachloropyridine | mol | 0.92 | 0.96 | 0.93 | 0.95 | 0.97 |
| Purity of product | % | 98.2 | 99.6 | 98.5 | 100 | 100 |
| Collected hydrogen chloride during distillation | mol | 1.0 | 1.0 | 1.0 | 1.0 | 1.0 |

EXAMPLE 4

Preparation of 2,3,5,6-tetrachloropyridine

In the following experiments the improved process b. of the invention for the preparation of 2,3,5,6-tetrachloropyridine is illustrated.

As starting materials in the experiments described use is made of a mixture of 1.0 mol of 3,3,5-trichloroglutarimide, 2.0 mol of phosphorus trichloride and 2.0 mol of phosphorus oxytrichloride.

The starting materials are mixed in a 1 liter autoclave as outlined in FIG. 1 of the drawings and heated to the reaction temperature.

Through a submerged pipe in the autoclave chlorine is supplied at the reaction temperature.

After the supplying of chlorine is complete, the outlet to the hydrogen chloride absorber is closed and the reaction mixture is heated at between 160° C. og 200° C. During the heating and at the reaction temperature hydrogen chloride formed is vented to the scrubber.

Thereafter the reaction mixture is cooled to about 50° C. and through the submerged pipe chlorine is supplied from a pressurized cylinder.

After the metering of chlorine is complete, the reaction mixture is heated at reflux for 1 hour. Thereafter phosphorus oxytrichloride is distilled off at atmospheric pressure to a bottom temperature of about 140° C.

Vacuum is gradually applied to the system while continuously distilling off phosphorus oxytrichloride. At a vacuum of about 20 mm Hg and a continued bottom temperature of 140° C. the 2,3,5,6-tetrachloropyridine is distilled off.

While distilling off product there is cooled with oil at a temperature of 100° C. to prevent the product from crystallizing.

11

Moreover, concerning the autoclave arrangement for the preparation of 2,3,5,6-tetrachloropyridine as shown in FIG. 1 of the drawings the following should be remarked:

The back-pressure valve can be set to open at pressures of between 10 and 15 bars (gauge).

While supplying chlorine, valves 1, 2, 4 and 5 are open, and valve 3 is closed.

While heating to the dehydrogenation temperature of between 160° C. og 200° C., valves 1, 2, 3 and 4 are closed, and valve 5 is open.

While supplying chlorine, valves 1, 2, 4 and 5 are open, and valve 3 is closed. While distilling off phosphorus trichloride and phosphorus oxytrichloride, valves 2, 3 and 5 are open, and valves 1 and 4 are closed. While distilling off tetrachloropyridine (vacuum distillation), valves 2 and 3 are open, and valves 1, 4 and 5 are closed.

During the reaction—up to distilling off tetrachloropyridine—the condenser is cooled with oil at 0° C.

While distilling off tetrachloropyridine there is cooled with oil at 100° C.

The results of 5 experiments with varying chlorine ratios during the two chlorination steps and varying reaction temperatures are shown in the following Table 2.

As will appear from Table 2, 2,3,5,6-tetrachloropyridine is obtained by process b. of the invention in a high yield and with high purity.

TABLE 2

|  |  | Experiment | | | | |
| --- | --- | --- | --- | --- | --- | --- |
|  |  | 1 | 2 | 3 | 4 | 5 |
| Chlorine consumption during first part of chlorination | mol | 1.2 | 1.5 | 1.8 | 1.8 | 1.8 |
| Reaction temperature during first part of chlorination | °C. | 50 | 50 | 50 | 75 | 100 |
| Reaction temperature during dehydro-chlorination | °C. | 160 | 170 | 180 | 190 | 200 |
| Residence time during dehydro-chlorination | hours | 3 | 3 | 3 | 3 | 3 |
| Reaction pressure in the dehydro-chlorination | bars (gauge) | 15 | 15 | 15 | 15 | 15 |
| Chlorine consumption during second part of chlorination | mol | 0.8 | 0.5 | 0.2 | 0.2 | 0.2 |
| Reaction temperature during second part of chlorination | °C. | 50 | 50 | 50 | 50 | 50 |
| Distilled off: |  |  |  |  |  |  |
| phosphorus tri-chloride | mol | 0 | 0 | 0 | 0 | 0 |
| phopshorus oxy-trichloride | mol | 3.8 | 3.8 | 3.8 | 3.8 | 3.8 |
| 2,3,5,6-tetra-chloropyridine | mol | 0.95 | 0.96 | 0.97 | 0.96 | 0.95 |
| Purity of product | % | 98.5 | 99.6 | 100 | 99.8 | 99.4 |

EXAMPLE 5

Preparation of 2,3,5,6-tetrachloropyridine

In the following experiment the improved process b. of the invention for the preparation of 2,3,5,6-tetrachloropyridine is illustrated.

In the experiment described the preparation of 2,3,5,6-tetrachloropyridine is carried out continuously by an embodiment as described in Example 4.

12

A continuous laboratory plant is outlined in FIG. 2 of the drawings.

To a 2 liter reaction flask 24 with a side branch, mechanical stirrer, thermometer and reflux condenser the following is metered per hour:

433.0 g [2.0 mol] of 3,3,5-trichloroglutarimide through a solids metering funnel 26, which is supplied with a weak nitrogen current to prevent hydrogen chloride from the reaction from passing up into the solids metering screw.

A mixture of 614.0 g [4.0 mol] of phosphorus oxytrichloride and 550.0 g [4.0 mol] of phosphorus trichloride through a piston pump 28.

120.7 g [1.7 mol] of chlorine as a gas through a submerged pipe 29.

The temperature in the reaction flask is maintained at between 50° C. and 70° C. by means of cooling water. The degasing from the reaction is cooled in the reflux condenser with cold (about 5° C.) oil before it is passed to a hydrogen chloride absorber.

The reaction mixture flows from the reaction flask into a metering funnel 30 from which it is pumped by means of a high-pressure piston pump 32 into a 2 liter autoclave 10.

The temperature in the autoclave is maintained between 160° C. and 200° C., preferably between 170° and 190° C.

During the residence in the autoclave hydrogen chloride is formed which is vented through a back-pressure valve in the top of a oil cooler mounted on the autoclave.

The back-pressure valve has been set to maintain a pressure of about 15 bars (gauge) in the autoclave.

The hydrogen chloride formed is passed to an absorber.

From a submerged pipe 34 in the autoclave the reaction mixture is withdrawn via an oil cooler 36 and a control valve to another reaction flask 38 with a side branch, mechanical stirrer, thermometer and reflux condenser.

The withdrawal of the reaction mixture from the autoclave is controlled such that the level in the autoclave is maintained fairly constantly at about ¾ charging.

To the last reaction flask there is supplied per hour:

21.3 g [0.3 mol] of chlorine as a gas through a submerged pipe 40.

The temperature in the reaction flask is maintained at between 70° C. and 100° C. by means of cooling water. The degasing from the reaction is cooled in the reflux condenser 42 with cold (about 5° C.) oil before it is passed to a hydrogen chloride absorber.

The reaction mixture flows from the reaction flask into a metering funnel 44 from which it is pumped by means of a piston pump 46 into a receiving vessel.

The work up of the reaction mixture takes place by a batch distillation as described under Examples 3 and 4.

After running-in the continuous laboratory plant so that the plant is in equilibrium, in an operation period of 6 hours 9806 g of reaction mixture is collected for distillation. During the distillation of this mixture the following is collected:

39.4 g [1.08 mol] of hydrogen chloride, 7089.8 g of phosphorus oxytrichloride having a content of 0.23% of phosphorus trichloride corresponding to 46.08 mol of phosphorus oxytrichloride and 0.12 mol of phosphorus trichloride.

2538.6 g of 2,3,5,6-tetrachloropyridine having a purity of 99.5%, corresponding to 11,6 mol [A yield percentage of 97.0].

The distillation residue, constituting 87,5 g (which is a difference between collected reaction mixture and the various fractions of 50,7 g), contains 3.1% of 2,3,5,6-tetrachloropyridine.

We claim:

1. A process for the preparation of 2,3,5,6-tetrachloropyridine of formula I

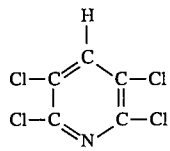

by reacting 3,3,5-trichloroglutarimide of formula II

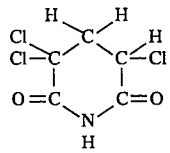

with phosphorus trichloride and chlorine, optionally in the presence of phosphorus oxytrichloride as a solvent, followed by a dehydrochlorination of the reaction mixture and finally conversion of polyphosphorus compounds formed into phosphorus oxytrichloride by supplying chlorine optionally only after supplying further phosphorus trichloride.

2. A process according to claim 1, comprising using a mixture of 2 moles of phosphorus trichloride and 2 moles of phosphorus oxytrichloride per mole of 3,3,5-trichloroglutarimide.

3. A process according to claim 1, comprising using, in the first part of the chlorination reaction, an amount of between 1.2 and 1.8 moles of chlorine per mole of 3,3,5-trichloroglutarimide used.

4. A process according to claim 1, comprising using, in the first part of the chlorination reaction, at least as many moles of phosphorus trichloride as those of chlorine.

5. A process according to claim 1, wherein the first part of the chlorination reaction is carried out at a temperature of between 20° C. and 100° C.

6. A process according to claim 1, wherein the subsequent dehydrochlorination reaction is carried out at a temperature of between 160° C. and 200° C.

7. A process according to claim 1, comprising venting the hydrogen chloride formed during the dehydrochlorination reaction such as to maintain the pressure during the reaction at between 10 and 15 bars (gauge).

8. A process according to claim 1, further comprising adding further phosphorus trichloride after the dehydrochlorination reaction such as to use a total of at least 2 moles of phosphorus trichloride per mole of 3,3,5-trichloroglutarimide.

9. A process according to claim 1, wherein after the dehydrochlorination reaction and optional addition of further phosphorus trichloride, chlorine is supplied in an amount such as to use a total of 2 moles of chlorine per mole of 3,3,5-trichloroglutarimide used.

10. A process according to claim 1, wherein the last part of the chlorination reaction is carried out at a temperature of between 20° C. and 100° C.

11. A process according to claim 3, wherein said amount is between 1.6 and 1.8 moles.

12. A process according to claim 5, wherein said temperature is between 50° C. and 70° C.

13. A process according to claim 6, wherein said temperature is 180° C.

14. A process according to claim 10, wherein said temperature is between 70° C. and 100° C.

* * * * *